United States Patent [19]

Meilland, deceased

[11] Patent Number: Plant 6,804

[45] Date of Patent: May 16, 1989

[54] ROSE PLANT — MEIPLOVON VARIETY

[75] Inventor: Marie-Louise Meilland, deceased, late of Antibes, France, by Jean-Pierre Le Naour, legal representative

[73] Assignee: The Conard-Pyle Company, West Grove, Pa.

[21] Appl. No.: 136,383

[22] Filed: Dec. 22, 1987

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms in abundance distinctive elegant well-formed semi-double neyron pink blossoms of long vase life. The plant exhibits vigorous vegatation and is well suited for cut flower production. Good resistance to fungal diseases is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the product of the pollination of the Meialfi variety by an unnamed seedling wherein the resulting offspring was crossed by the offspring of the Golden Garnet variety and an unnamed seedling. The male parent (i.e., the pollen parent) of the new variety was the Samantha variety (U.S. Plant Pat. No. 3,727). The parentage of the new variety can be summarized as follows:

$$\left[\text{MEIALFI} \times \text{unnamed seedling}\right] \times \left[\text{GOLDEN GARNET} \times \text{unnamed seedling}\right] \times \text{SAMANTHA.}$$

The seeds resulting from the above pollination were sown and 88 plantlets were obtained which were physically and biologically different from each other. Selective study resulted in the identification of a single plant of the new variety.

It was found that the new variety of Hybrid Tea rose plant of the present invention possesses the following combination of characteristics:

(a) forms in abundance elegant semi-double neyron pink blossoms which retain their color well when cut and present in a vase,
(b) exhibits an erect growth habit,
(c) forms vigorous vegatation, and
(d) exhibits good resistance to cryptogamic diseases.

The new variety well meets the needs of the horticultural and is particularly well-suited for the production of cut flowers.

The new variety has been found to undergo asexual propagation by a number of routes, including budding, grafting, cutting, etc. The characteristics of the new variety have been found to be strictly transmissible by such asexual propagation from one generation to another.

The new variety has been named the Meiplovon variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and observed during June while grafted on *Rosa indicia* understock and growing in a greenhouse at Cap d'Antibes, France.

DETAILED DESCRIPTION

Figures 1, 2, 3, 4, 5, 6, 7, 8, 9, 10, 11, 12, 13, 14, 15, 16, 17:
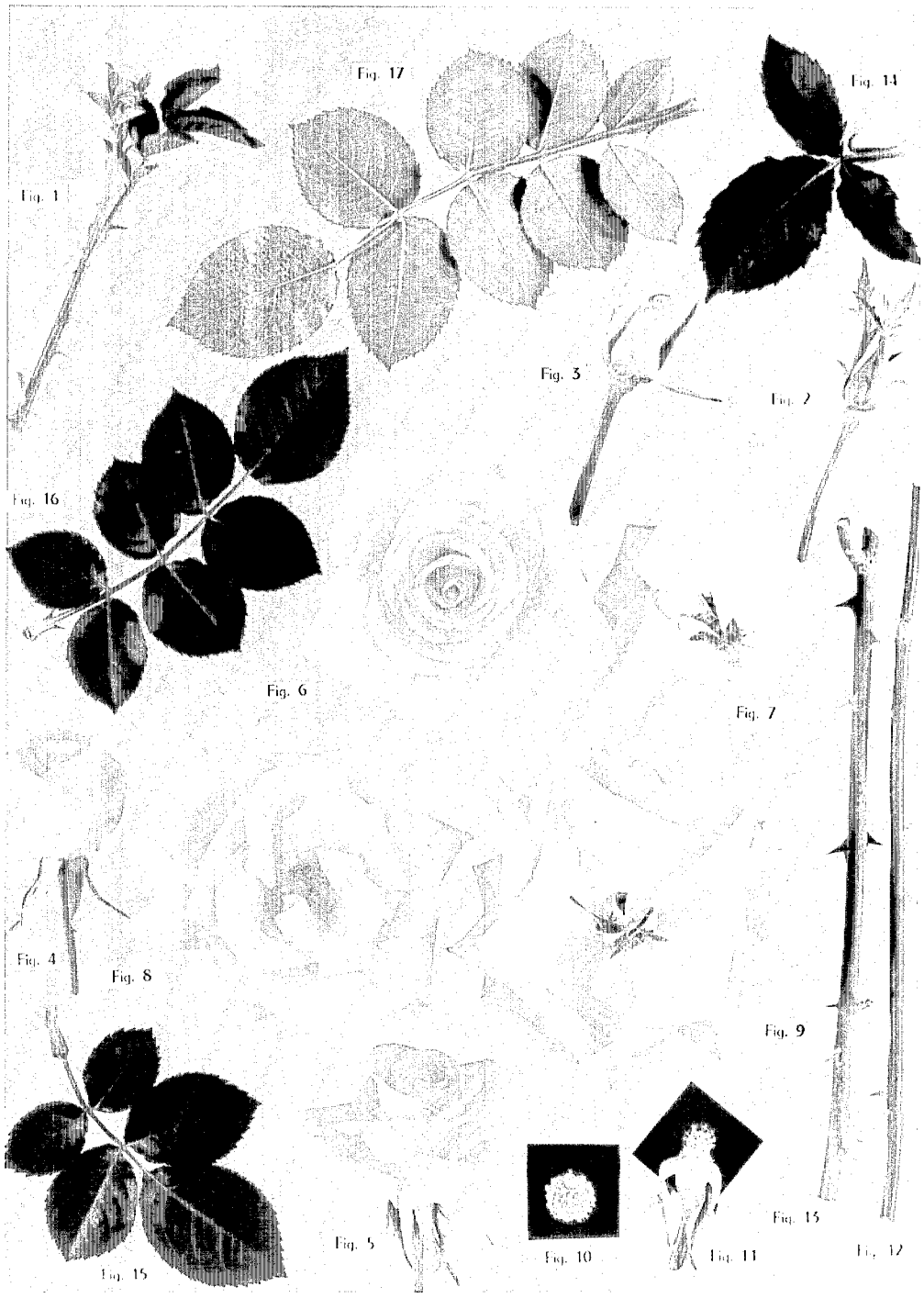
FIG. 1 illustrates a specimen of a young shoot.
FIG. 2 illustrates a specimen of a floral bud before the opening of the sepals.
FIG. 3 illustrates a specimen of a floral bud before the petals open.
FIG. 4 illustrates a specimen of a floral bud when the petals open.
FIG. 5 illustrates a specimen of a flower in the course of opening.
FIG. 6 illustrates a specimen of a fully open flower — plan view — obverse.
FIG. 7 illustrates a specimen of a fully open flower — plan view — reverse.
FIG. 8 illustrates a specimen of a fully open flower immediately prior to petal drop — plan view — obverse.
FIG. 9 illustrates a specimen of a fully open flower immediately prior to petal drop — plan view — reverse.
FIG. 10 illustrates a specimen of a floral receptacle showing the arrangement of the stamens and pistils (sepals removed)
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a leaf with three leaflets — plan view — upper surface.
FIG. 15 illustrates a specimen of a leaf with five leaflets — plan view — upper surface.
FIG. 16 illustrates a specimen of a leaf with seven leaflets — plan view — upper surface.
FIG. 17 illustrates a specimen of a leaf with nine leaflets — plan view — under surface.

The chart used in the identification of the colors is that of The Royal Horticultural Society (R.H.S. Colour Chart). The description is based on observations of two year old specimens made during June while grafted on *Rosa indicia* understock and growing in a greenhouse at Cap d'Antibes, France. Color terminology in common terms precedes the reference to such chart.

Class: Hybrid Tea.

Plant:

*Height.*—Plants which were pruned to a height of 85 cm. commonly product floral stems having a length of approximately 40 to 60 cm. The floral stems commonly are of variable lengths.

*Habit.*—Erect.

Branches:

*Color.*—Young stems: lettuce green, Yellow-Green Group 144A. Adult wood: bronzed green, Yellow-Green Group 146A.

Leaves:

*Stipules.*—Adnate, pectinate, wide and linear.

*Petioles.*—Upper surface: grooved, reddish brown on young foliage and medium green on adult foliage with glandular edges intermingled with small aciculas. Under surface: light green, bear some small hooked thorns.

*Leaflets.*—Number: 3, 5, 7 (most often), and 9. Often the first two leaves have only one leaflet. Shape: Oval. Serration: simple and regular. Texture: very firm. General appearance: dark green ample foliage with semi-glossy effect. Color (young foliage): upper surface: reddish brown. under surface: reddish brown. Color (adult foliage): upper surface: dark green, Yellow-Green Group 147A. under surface: light green, Yellow-Green Group 147B.

Inflorescence:

*Number of flowers.*—Generally one per stem.

*Peduncle.*—Straight, rigid, and light green in coloration, approximately 6.5 cm. in length on average.

*Sepals.*—Upper surface: tormentose, greenish in coloration with more or less glandular edges. Under surface: medium green in coloration, the outside sepals have edges which are more or less appendiculated, the end portion is more or less suffused with a reddish tint.

*Buds.*—Shape: oblong. Length: approximately 3 cm. on average. Size: average. Color upon opening: upper surface: dark carmine pink, Red Group 52A. under surface: carmine pink, Red Group 52B.

*Flowers.*—Shape: when opening the petals have parallel edges which upon the passage of time assume the configuration of a hollow cup. Diameter: approximately 11 cm. on average. Color (when opening begins): upper surface: neyron pink, Red Group 55A and lighter on the edges of the petals. under surface: neyron pink, Red Group 55B and lighter on the edges of the petals. Color (when blooming): upper surface: neyron pink, Red Group 55B and slightly lighter on the edges of the petals. under surface: neyron pink, Red Group 55B. Color (at end of opening): upper surface: neyron pink, Red Group 55B and lighter on the outside petals. under surface: neyron pink, Red Group 55B and lighter on the outside petals. Fragrance: light. Lasting quality: long. Petal number: approximately 24 on average. Petal form: generally rounded. Texture: firm. Petal drop: good. Stamen number: approximately 97 on average. Anthers: normal, ochre in coloration. Filaments: golden yellow in coloration, of irregular heights. Pistils: approximately 86 on average. Stigmas: normal, straw yellow in coloration. Styles: dark fuchsine in coloration with a straw yellow base, sometimes two are joined, of irregular heights. Receptacle: light green in coloration at the dehiscence of the anthers and in longitudinal section wide and jug shaped.

Developement:

*Vegetation.*—Vigorous.

*Blooming.*—Abundant.

*Aptitude to forcing.*—Good.

*Resistance to diseases.*—Good.

It is claimed:

1. A new and distinct variety of Hybrid Tea rose plant characterized by the following combination of characteristics:

(a) forms in abundance elegant semi-double neyron pink blossoms which retain their color well when cut and present in a vase, (b) exhibits an erect growth habit, (c) forms vigorous vegatation, and (d) exhibits good resistance to cryptogamic diseases; substantially as herein shown and described, together with the parts thereof.

* * * * *